United States Patent [19]

Cumming

[11] Patent Number: 4,976,716
[45] Date of Patent: Dec. 11, 1990

[54] INTRAOCULAR LENS INSERTION DEVICE

[76] Inventor: J. Stuart Cumming, #201 1211 W. LaPalma Ave., Anaheim, Calif. 92081

[21] Appl. No.: 298,925

[22] Filed: Jan. 23, 1989

[51] Int. Cl.$^5$ .............................................. A61B 17/00
[52] U.S. Cl. .................................................... 606/107
[58] Field of Search ........................................ 606/107

[56] References Cited

U.S. PATENT DOCUMENTS 4,715,373 12/1987 Mazzocco et al. ................. 606/107

Primary Examiner—Michael H. Thaler
Attorney, Agent, or Firm—Boniard I. Brown

[57] ABSTRACT

An improved surgical instrument having lens gripping fingers straddled by backup fingers for implanting a foldable intraocular lens in a patient's eye by (a) closing the backup fingers to close the gripping fingers with an unfolded lens positioned between slender tip portions of the gripping fingers in such a way that the lens is folded and gripped between the tip portions, (b) inserting the gripping finger tip portions and the folded lens into the eye thru a corneal incision, (c) extending the gripping fingers beyond the backup fingers and further into the eye to free the tip portions for gradual separation by the elastic strain energy in the folded lens and thereby free the lens to gradually unfold, (d) pushing the unfolding lens from the gripping fingers to release the lens to unfold to its normal lens configuration within the eye, and (e) retracting the gripping fingers relative to the backup fingers and then withdrawing the instrument from the eye. The preferred surgical instrument embodies a disposable lens insertion capsule assembly including the lens gripping fingers and a reusable capsule holder including the backup fingers. A surgical aid in the form of a sterilizable instrument package containing a tray supporting an unfolded lens to be implanted and either the complete surgical instrument or the insertion capsule assembly only with which the capsule holder is engagable on the tray to form the complete instrument after the package is opened.

23 Claims, 5 Drawing Sheets

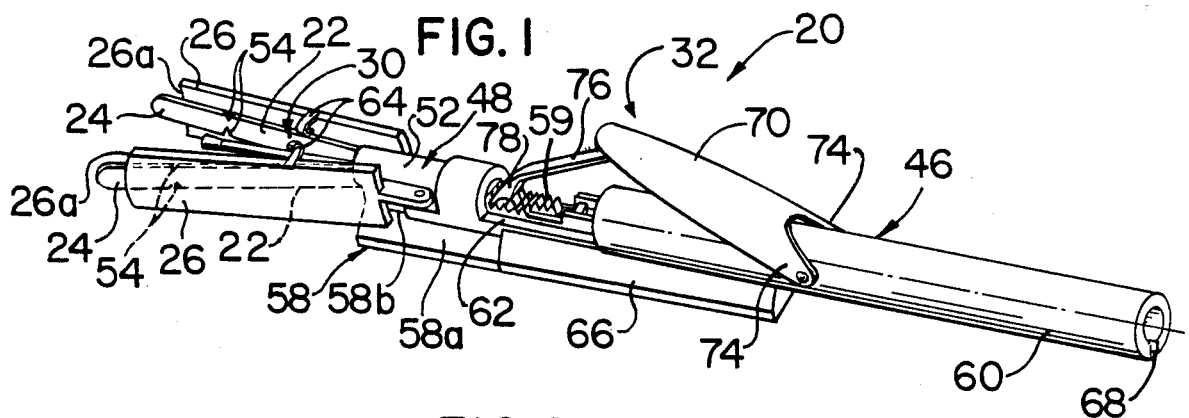
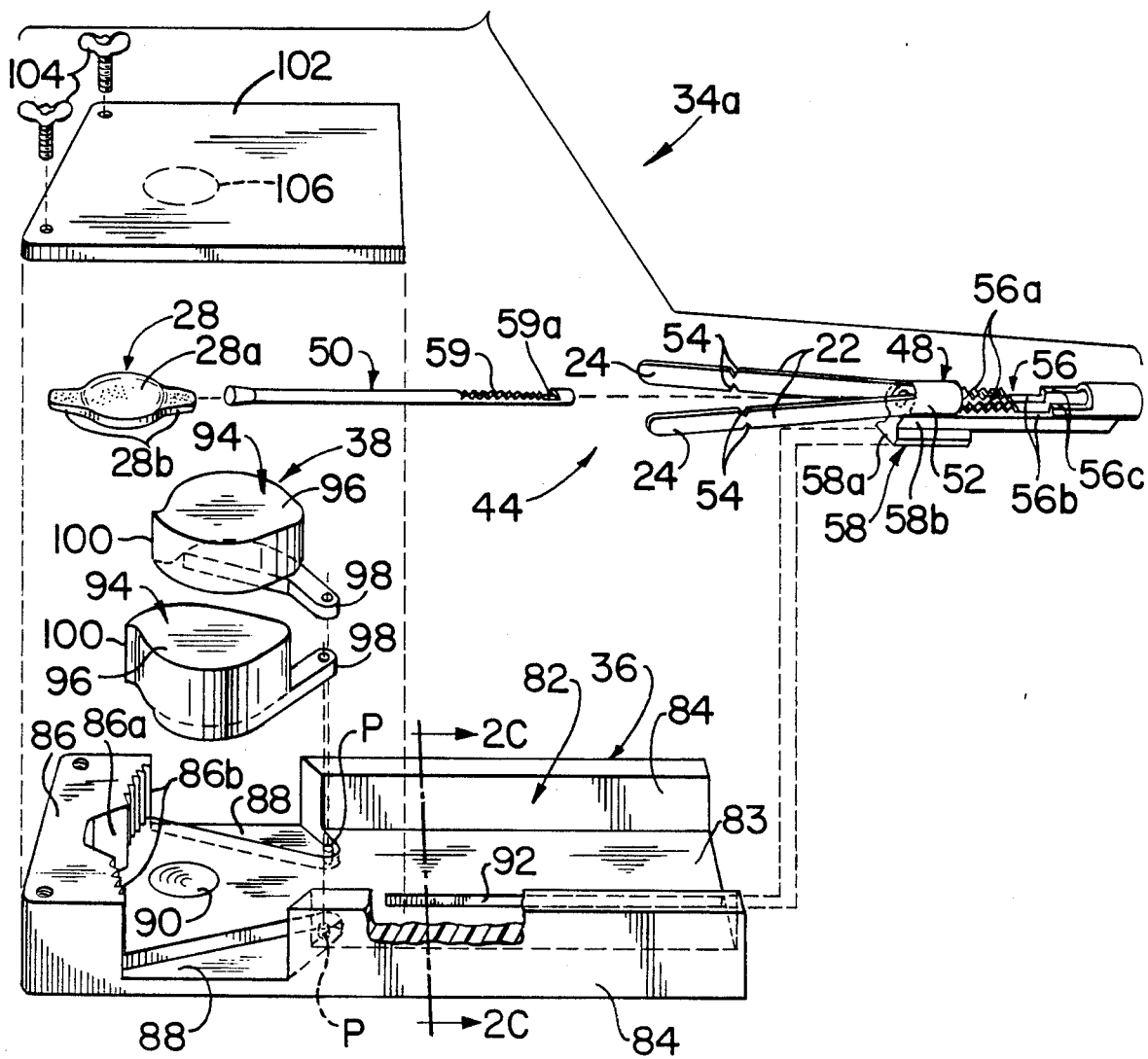

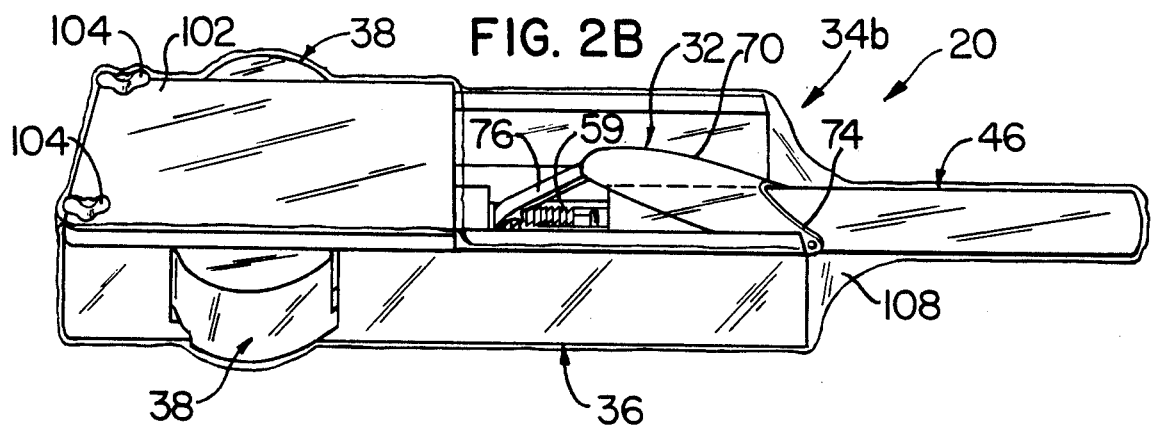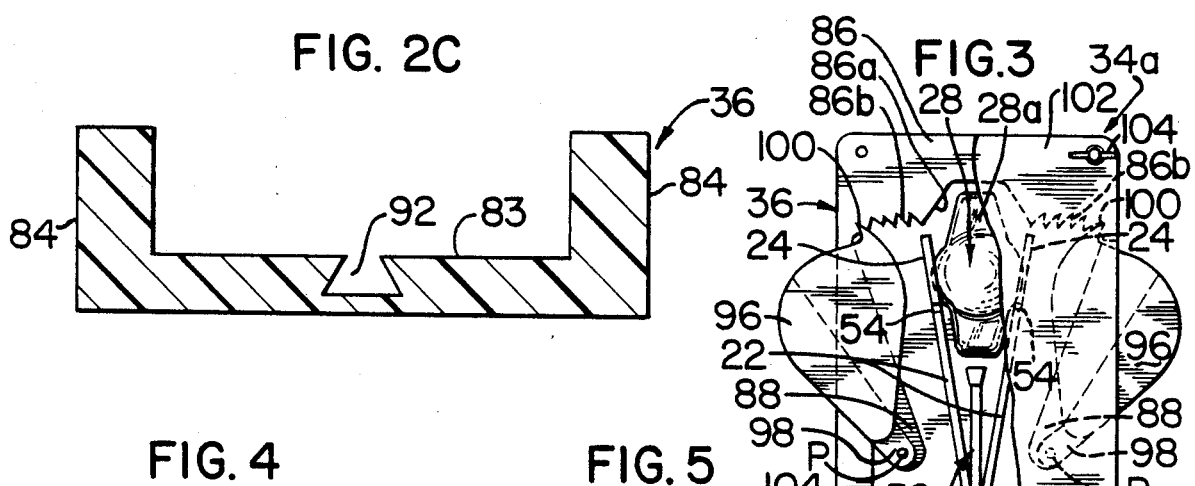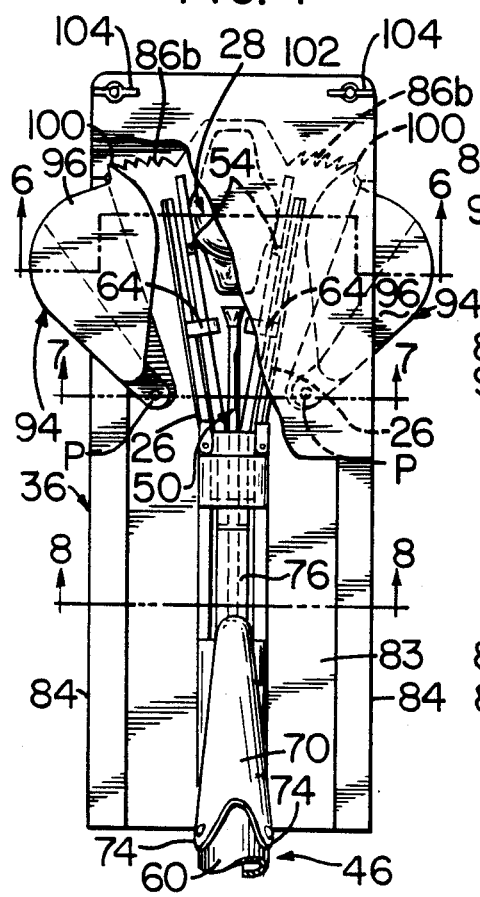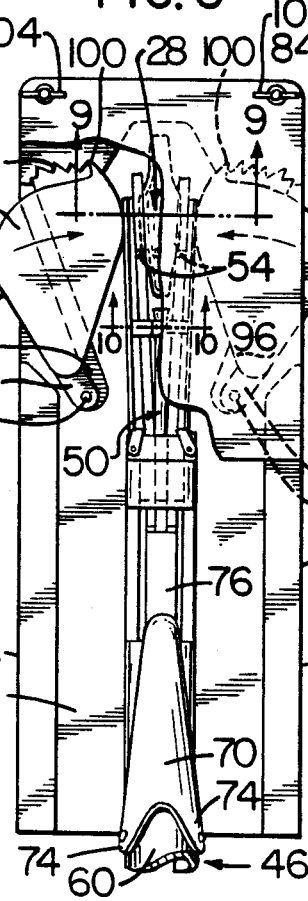

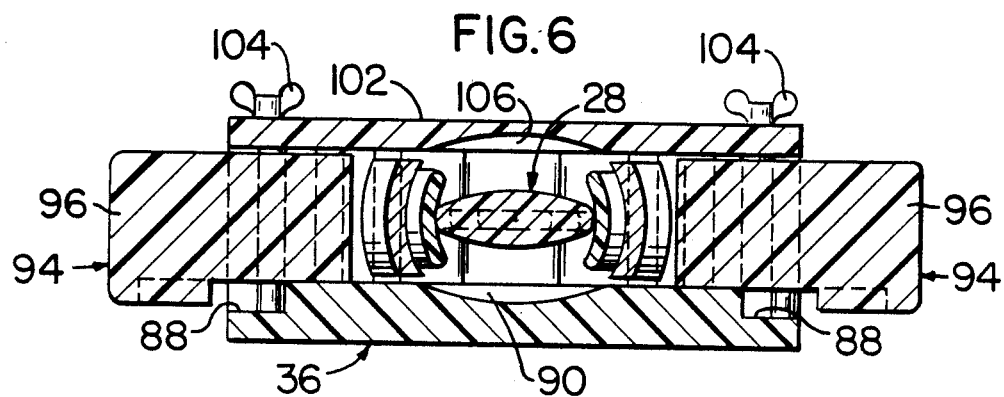
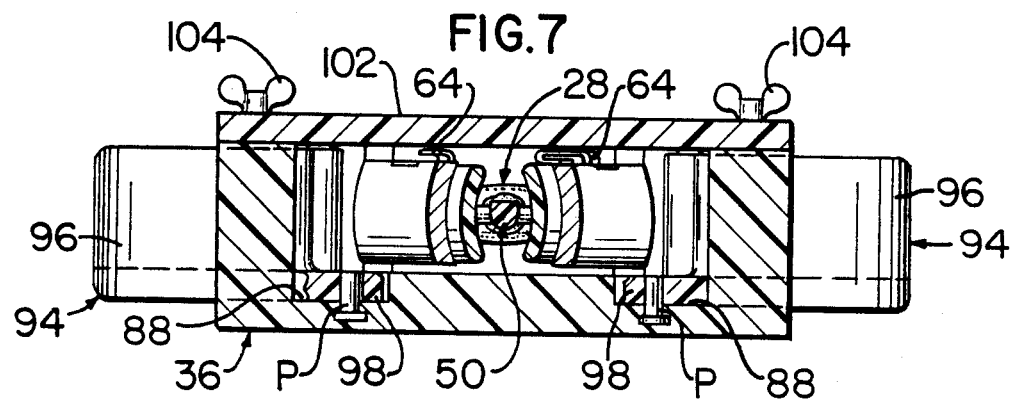
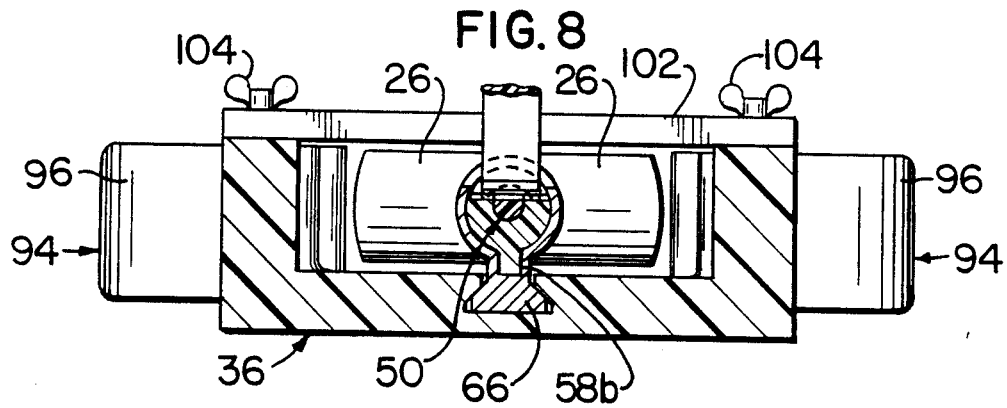
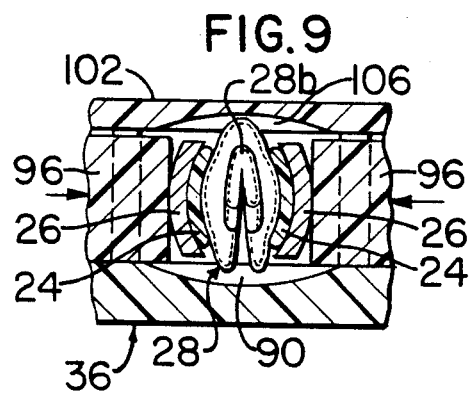
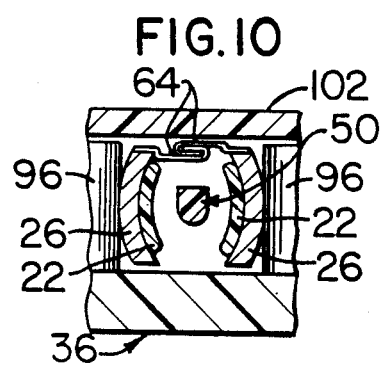

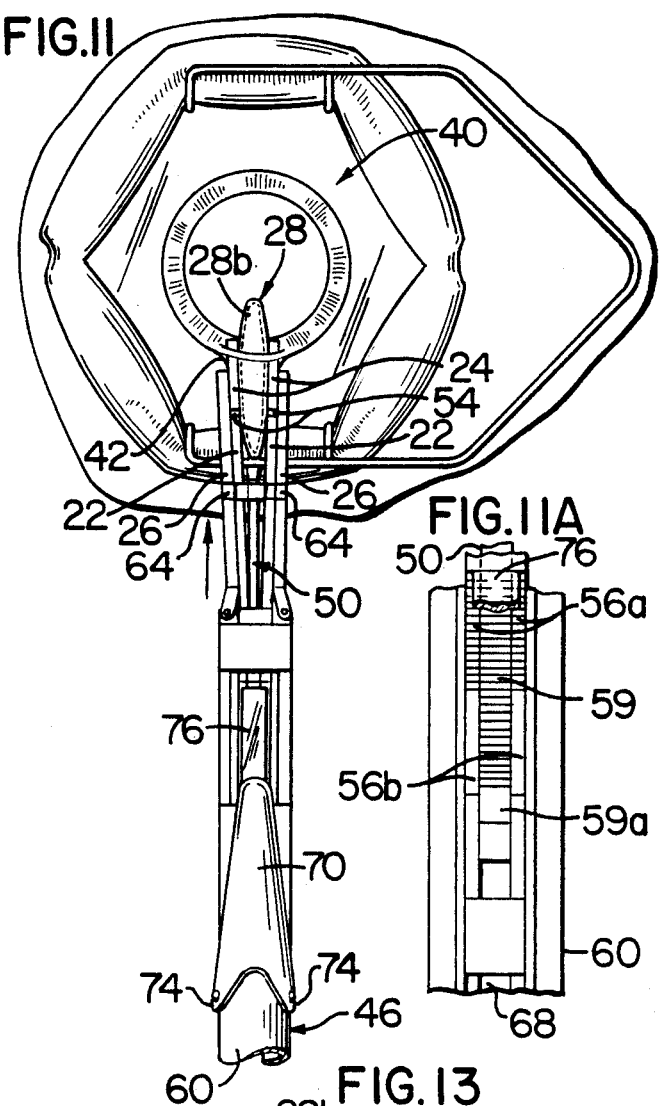
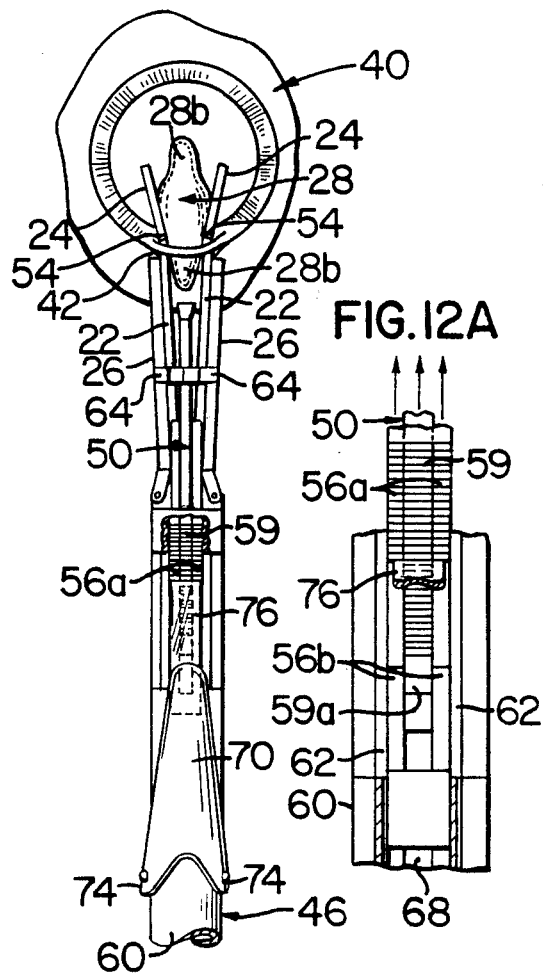
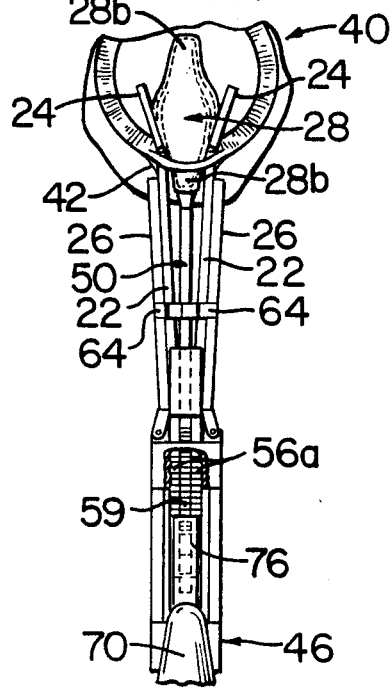
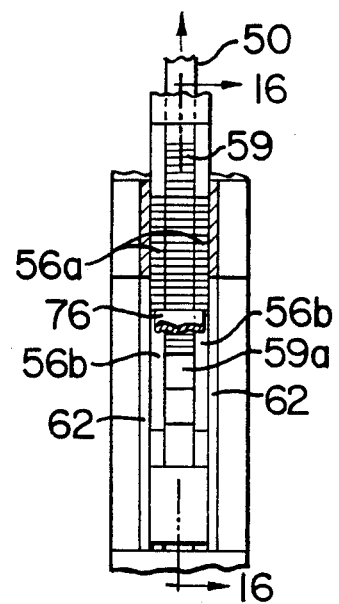

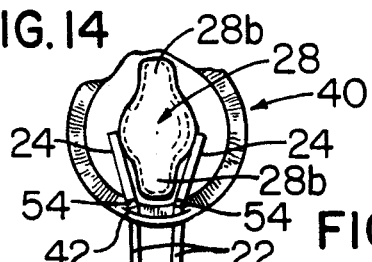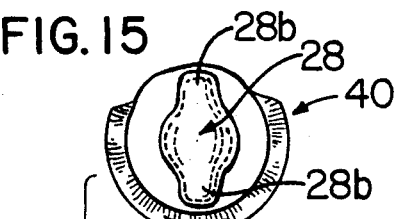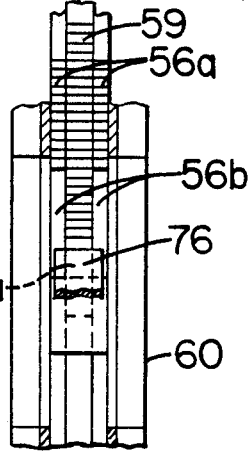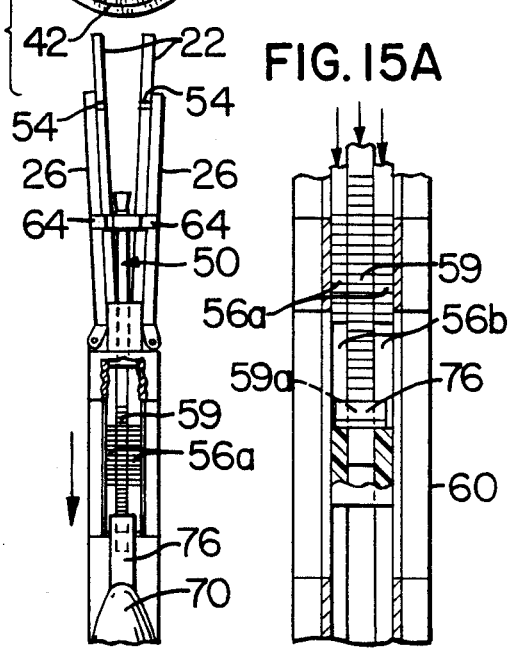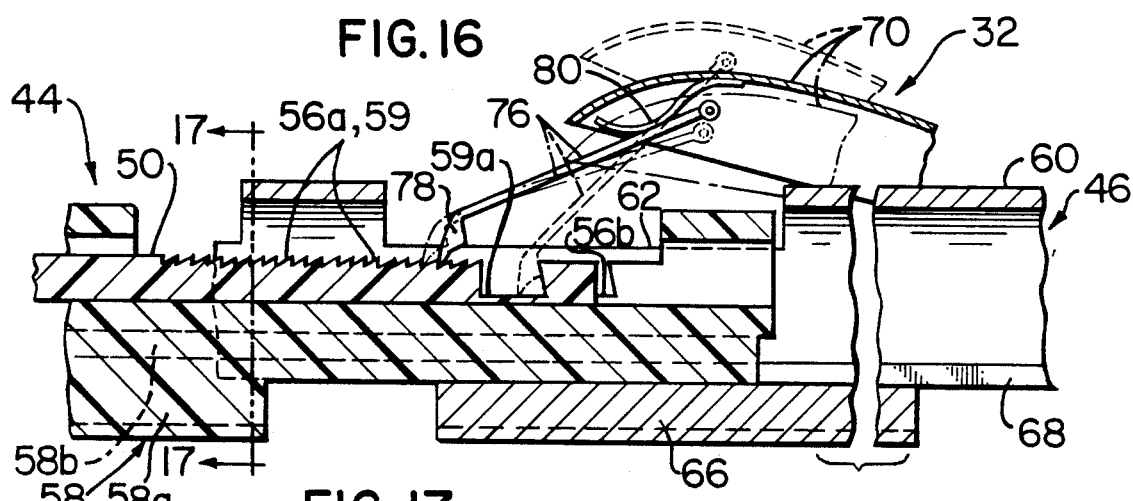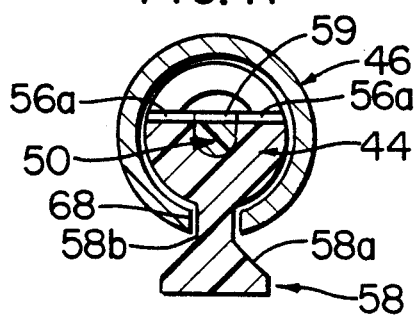

INTRAOCULAR LENS INSERTION DEVICE

BACKGROUND OF THE INVENTION

Field Of The Invention

1. This invention relates generally to art of intraocular lens implantation and more particularly to a novel surgical aid including an improved surgical instrument and surgical instrument package for inserting a foldable intraocular lens into a patient's eye thru a corneal incision.

Discussion Of The Prior Art

2. The lens of the human eye is a crystalline lens which is situated behind the iris and attached to the ciliary muscle by zonules. The lens consists of an outer capsule with anterior and posterior surfaces, the lens containing a clear central matrix. This central matrix often opacifies with age and for various other reasons and thereby progressively blocks the passage of light to the retina of the eye. Eventually, the central matrix attains a degree of opacity which is referred to as a cataract. This abnormal ocular condition is corrected by removing the opacacified lens, which is a procedure known as cataract extraction, and replacing the lens by an artificial lens for focusing the light entering the eye on the retina. Intraocular lenses have gained widespread acceptance as replacements for cataracted human lenses.

The modern technique for removing the central opaque part of the lens or cataract is a procedure called phacoemulsification. In this procedure, a sophisticated ultrasonic titanium tipped instrument is introduced into the eye. This titanium tip is ultrasonically vibrated in a manner which emulsifies the opaque central matrix of the lens. The emulsified matrix is then aspirated from the eye, leaving the original posterior capsule of the lens intact with a small anterior capsular remnant. When the capsule or part of the capsule is thus left inside the eye, the procedure is called extracapsular cataract extraction. Extra capsular extraction allows the intraocular lens to be placed behind the iris either in the space known as the ciliary sulcus, that is the space immediately behind the iris and in front of the anterior capsule remnant or in a space known as the capsular bag, that is between the posterior surface of the anterior capsular flap and the anterior surface of the posterior capsule.

A cataract can be removed by this phacoemulsification procedure through an incision of 3 mm or less. On the other hand, most intraocular lenses implanted today are hard methyl methacrylate lens having a diameter of at least 6 mm and as much as 7 mm or 8 mm. Therefore, the incision used for the phacoemulsification procedure has to be enlarged to more than twice its size to allow the surgeon to implant a hard methyl methacrylate lens. Regarding the incision size, it is apparent to many leading cataract surgeons that the smaller the wound, the lower the complication rate during cataract surgery and the faster the physical and visual rehabilitation. The degree of astigmatism is also much less with the smaller wound.

The latest developments in intraocular lens technology have been in the area of deformable lenses made from silicone and hydroxyethylmethylmethacrylate materials. Intraocular lens fabricated from these materials can be deformed so that they may be inserted through a much smaller incision than those required for implantation of a hard, rigid intraocular lens. Foldable intraocular lenses of this kind and instruments for inserting such lenses into the eye are disclosed in U.S. Pat. No. 4,424,597 to Schlegel, U.S. Pat. No. 4,573,998 to Mazzoco, and U. S. Pat. No. 4,673,406 to Schlegel.

Although U.S. Pat. No. 4,573,998 to Mazzocco describes many different methods and instruments for inserting a foldable silicone lens through a small incision, these and the many other intraocular lens insertion methods and instruments which have been developed are by and large unsatisfactory. Thus, many of the instruments designed to insert a foldable lens damage the lens during insertion or are unable to fold the lens adequately to allow it to be inserted through a significantly smaller incision than that required for hard lenses.

Accordingly, there is a definite need for an improved surgical instrument for inserting or implanting a foldable intraocular lens into a patient's eye which avoids the above and other deficiencies of the existing surgical instruments for this purpose. My copending application Ser. No. 198,571 now U.S. Pat. No. 4,862,885 discloses one such improved surgical instrument for implanting a foldable intraocular lens.

SUMMARY OF THE INVENTION

According to one of its aspects, the present invention provides a further improved surgical instrument for the purpose described. This further improved instrument is constructed and arranged to fold a foldable intraocular lens without damaging the lens and into a sufficiently small effective crossection to permit insertion of the lens into a patient's eye by the instrument thru a small corneal incision such as that used for cataract extraction by the phacoemulsification procedure. According to another aspect, the invention provides a novel surgical, foldable intraocular lens implantation aid in the form of a sterile surgical instrument package. This instrument package includes a tray for supporting the improved surgical instrument of the invention and a foldable intraocular lens in its normal unfolded configuration. The instrument package is manipulatable by the surgeon or an assistant, directly in the operating room and immediately before the lens implantation, to cause the instrument to fold and grip the lens without the surgeon or assistant touching the lens and while the instrument and lens are still on the tray. The instrument and its gripped folded lens are then removed from the tray for use by the surgeon to insert the lens into the eye.

Simply stated, the improved surgical, lens insertion instrument of the invention has lens gripping members with very slender lens gripping portions which are sized for insertion thru a small corneal incision. These lens gripping members are movable away from one another to open positions wherein their gripping portions are spaced to straddle a foldable intraocular lens in its normal unfolded configuration and toward one another to closed positions to deform or fold the lens to a compact folded configuration and then grip the lens to retain it in this folded configuration. Straddling the lens gripping members are relatively rigid backup members. These backup members are movable away from one another to open positions wherein the backup members are spaced to straddle the gripping members in their open positions and toward one another to close the gripping members and then support these gripping members in their closed positions. Also included in the instrument are means for securing the backup members and thereby also the lens gripping members in their closed positions and actuating means operable by the surgeon using the instrument for extending the gripping members beyond the backup members into the patient's eye and then releasing the folded lens from the lens gripping members into the eye. When thus released, the lens unfolds to its normal lens configuration within the eye by the elastic strain energy stored in the folded lens.

The improved lens insertion instrument is used by closing its backup members to close the lens gripping members about an unfolded intraocular lens positioned between the gripping members in such a way that the lens is folded and the folded lens is then gripped between the gripping portions of the gripping members. The backup member securing means then secures the backup members and thereby also the gripping members in their closed positions, preferably with the lens gripping portions of the gripping members projecting beyond the backup members. In this initial closed, lens gripping configuration of the instrument, the lens gripping portions of the gripping members and the folded lens gripped thereby present a very small effective cross-section which permits insertion the gripping portions and the folded lens into a patient's eye thru a corneal incision of the size, i.e. 3 mm or less, used for cataract extraction by the phacoemulsification procedure.

With a folded lens thus gripped by the instrument, the surgeon manipulates the instrument to insert the lens gripping portions of its lens gripping members and the gripped folded lens into the patient's eye thru the corneal incision used for cataract extraction. The surgeon then operates the actuating means of the instrument in a manner to effect gradual release of the folded lens from the instrument into the eye after which the instrument is withdrawn from the eye. When thus released, the elastic strain energy stored in the folded lens causes the lens to gradually unfold to its normal lens configuration in the eye. The lens may thus be inserted into either the ciliary sulcus or into capsular bag of the eye and will have appropriate haptics for positioning and supporting the lens in the eye. During insertion of the lens into the eye, one haptic preferably protrudes beyond the lens gripping portions of the instrument for initial entrance thru the corneal incision.

In its presently preferred form, the improved surgical instrument of the invention has two basic components, namely a disposable insertion capsule assembly and a reusable capsule holder which is releasibly engagable with the insertion capsule assembly to form the complete instrument. The disposable insertion capsule assembly includes an insertion capsule proper and a plunger. The insertion capsule has a tubular body slidably containing the plunger and a pair of very slender pivotal lens gripping fingers at one end of the body which constitute the lens gripping members of the instrument. The insertion capsule is preferably a one piece molded plastic part wherein the gripping fingers are resiliently bendable fingers integrally joined to the body and biased to normally assume their open positions. The reusable capsule holder has a tubular body pivotally mounting at one end a pair of relatively rigid backup fingers which constitute the backup members of the instrument. The capsule holder also embodies a capsule actuating pawl which is movably mounted on the holder body and constitutes one component of the capsule actuating means.

The disposable insertion capsule assembly and reusable capsule holder are assembled to form the complete lens insertion instrument by sliding the holder body over the tubular capsule body to locate its backup fingers in straddling relation to the insertion capsule gripping fingers. The insertion capsule body and plunger have ratchet teeth engagable by the capsule actuating pawl to extend and retract the capsule and plunger relative to the capsule holder. The backup finger securing means comprise coacting latch means on the backup fingers which engage when these fingers close to lock the backup fingers and thereby the lens gripping fingers in their closed positions. The instrument may be so constructed and arranged that when the backup and gripping fingers are thus closed, the tip portions of the gripping fingers either project or may thereafter be projected an initial distance beyond the free ends of the backup fingers.

This preferred lens insertion instrument of the invention is used by closing its backup and lens gripping fingers with an unfolded intraocular lens positioned between the tip portions of the gripping fingers in such a way that the gripping fingers fold the lens and then grip the folded lens between their tip portions with these tip portions projecting their initial distance beyond the backup fingers. These projecting tip portions of the gripping fingers and the gripped folded lens are then inserted into the patient's eye thru the incision in the cornea which was used for cataract extraction. While the gripping fingers and lens are thus inserted into the eye, the capsule actuating pawl is operated to sequentially (a) extend the insertion capsule and plunger in unison relative to the capsule holder to extend the tip portions of the capsule lens gripping fingers further beyond the backup fingers and into the eye to permit separation (i.e. opening) of the tip portions by the stored elastic strain energy in the folded lens and thereby effect release of the folded lens from the gripping fingers; (b) then extend the capsule plunger relative to the insertion capsule to nudge the lens from the separating gripping finger tip portions; (c) thereafter retract the plunger relative to the insertion capsule, and (d) finally retract the insertion capsule and plunger in unison relative to the capsule holder to reclose the gripping finger tip portions. The instrument is then withdrawn from the patient's eye, the insertion capsule assembly and capsule holder are separated, the capsule assembly is disposed of, and the capsule holder is saved for reuse.

The surgical aid of the invention includes a tray for supporting the improved surgical instrument and a foldable intraocular lens in its normal unfolded configuration in a position between the open lens gripping members or fingers of the instrument, and means for closing the backup members and thereby the lens gripping members of the instrument to fold and grip the lens while the instrument is on the tray. The instrument is then removed from the tray to implant the lens.

In one disclosed embodiment of the surgical aid, the lens insertion capsule assembly only and an unfolded lens are initially positioned on the tray to form an instrument package which is sterilized and sealed. In another disclosed embodiment, the sterile instrument includes the tray, lens, and complete surgical instrument. Each instrument package is intended to be opened in the operating room just before the lens is to be inserted. If the instrument package includes only the insertion capsule assembly, the capsule holder is engaged with the capsule assembly to form the complete insertion instrument after the package is opened and while the assembly is still on the tray. In either case, the backup members or fingers of the capsule holder are closed by closure members on the tray to close the lens gripping members or fingers of the capsule assembly and thereby fold and grip the lens on the tray. The insertion instrument is then removed from the tray to insert the folded lens gripped by the instrument lens gripping fingers.

BRIEF DESCRIPTION OF THE DRAWINGS

FIG. 1 is perspective view of a presently preferred surgical instrument according to the invention;

FIG. 2A is an exploded perspective view of an instrument package according to the invention which includes only the lens insertion capsule assembly of the surgical instrument;

FIG. 2B is a perspective view of a modified instrument package according to the invention, which includes the entire surgical instrument of FIG. 1;

FIG. 2C is a section taken on line 2C—2C in FIG. 2A;

FIG. 3 is a top plan view of an instrument package, which may be either the instrument package of FIG. 1 or the instrument package of FIG. 2A, in a certain condition of use;

FIGS. 4 and 5 are plan views similar to FIG. 3 illustrating closure of the of the lens gripping and backup members or fingers of the instrument;

FIG. 6 is an enlarged section taken on line 6—6 in FIG. 4;

FIG. 7 is an enlarged section taken on line 7—7 in FIG. 4;

FIG. 8 is an enlarged section taken on line 8—8 in FIG. 4;

FIG. 9 is an enlarged section taken on line 9—9 in FIG. 5;

FIG. 10 is an enlarged section taken on line 10—10 in FIG. 5;

FIGS. 11-15A illustrate successive steps involved in using the surgical instrument to insert a foldable intraocular lens into a patient's eye;

FIG. 16 is a section taken on line 16—16 in FIG. 13A;

FIG. 17 is a section taken on line 17—17 in FIG. 16.

DESCRIPTION OF THE PREFERRED EMBODIMENTS

As noted earlier, one important aspect of the invention is concerned with a surgical, foldable intraocular lens insertion instrument. FIG. 1 illustrates the instrument in its presently preferred configuration. This preferred instrument has a pair of lens gripping members 22 with very slender lens gripping portions 24 and relatively rigid backup members 26 straddling the gripping members. The lens gripping members 22 are movable away from one another to their open positions of FIG. 3 and toward one another to their closed positions of FIG. 5. In their open positions of FIG. 3, the gripping portions 24 of the lens gripping members 22 are spaced to straddle a foldable intraocular lens 28 in its illustrated normal unfolded lens configuration. During movement of the gripping members to their closed positions of FIG. 5, they fold the lens to its folded configuration illustrated in FIGS. 5 and 9 and then grip the folded lens. The backup members 26 are movable away from one another to their open positions of FIGS. 1 and 4 and toward one another to their closed positions of FIG. 5. In their open positions, the backup members are spaced to straddle the lens gripping members 22 in their open positions. During movement of the backup members to their closed positions, they engage and close the gripping members and then support the gripping members in their closed positions. Securing means 30 are provided for retaining the backup members 26 and thereby also the gripping members 22 in their closed positions with a folded lens 28 gripped between the gripping portions 24 of the gripping members. The instrument also includes actuating means 32 for extending the gripping members beyond the backup members 22 and releasing the gripped folded lens 28 from the gripping members.

As noted earlier, another important aspect of the invention is concerned with an instrument package which permits the surgeon or an assistant to use the surgical instrument of the invention in the operating room, immediately before a lens insertion operation, to fold and grip a foldable intraocular lens and then insert the newly folded lens into the eye. FIGS. 2A and 2B illustrate two different embodiments 34a and 34b of this instrument package. These instrument packages will be described in detail presently. Suffice it to say at this point that each package includes a tray 36 for supporting the lens insertion instrument 20 with its lens gripping members 22 and its backup members 26 open and supporting a foldable intraocular lens 28 in its normal unfolded lens configuration in a position between the gripping portions 24 of the gripping members. Mounted on the tray 36 are means 38 for closing the backup members 26 and thereby the gripping members 22.

Briefly, the surgical instrument 20 is used in the following manner assuming that the instrument and an unfolded lens 28 are initially positioned on the instrument package tray 36. First, the backup member closure means 38 on the tray are operated to close the backup members 22 and thereby the lens gripping members 22 of the instrument to fold and then grip the lens 28 while the instrument and lens are on the tray. The backup and gripping members are retained in their closed positions by the backup member securing means 30. The instrument 20 with the gripped folded lens is removed from the tray 36 and manipulated to first insert the lens into the patient's eye 40 thru a corneal incision 42, then release the lens from the instrument into the eye in such a way that the lens gradually unfolds to its normal lens configuration under the action of the stored elastic strain energy in the folded lens and finally withdraw the instrument from the eye.

Referring now in more detail to the drawings, the preferred surgical instrument has two major components, namely an insertion capsule assembly 44 and a capsule holder 46. The capsule assembly 44 includes an insertion capsule 48 proper and a plunger 50. Capsule 48 has a tubular body 52 and a pair of resiliently flexible fingers which are integrally joined to one end of and extend from the body at opposite sides of the body axis and constitute the lens gripping members 22 of the instrument. These lens gripping fingers 22 are arcuate in cross-section with facing concave sides and are stressed to normally assume their diverging positions of FIGS. 2A and 3 which are their open positions. The lens gripping fingers have tip portions which terminate at notches 54 in the edges of the fingers and constitute the lens gripping portions 24 of the fingers. One side of the capsule body 52, referred to herein as its upper side, has a cutout 56 defining longitudinal body edges having forward ratchet teeth 56a, central recesses 56b, and rear plateaus 56c. Depending from the underside of the capsule body 52 at its front end is a key 58 having a transverse crossection which is best shown in FIG. 17 and includes a lower tapered or dovetailed portion 58a and an upper rib-like portion 58b.

Plunger 50 is slidable within the capsule body 52 with its front end projecting between the capsule lens gripping fingers 22. This front end of the plunger is preferably somewhat enlarged, as shown, for reasons which will appear later. The rear end of the plunger has ratchet teeth 59 and a rear recess 59a which are exposed thru the capsule body cutout 56. For reasons which will appear from the later description, the row of plunger ratcher teeth 59 is longer than the rows of capsule ratchet teeth 56a.

The capsule holder 46 has a tubular body 60 which slidably receives the capsule body 52. In one side, referred to herein as its upper side, of the holder body 60 and adjacent one end of the body, referred to herein as its front end, is a cutout 62. Pivotally attached to and extending forwardly from the front end of the holder body 60 are a pair of relatively rigid fingers which constitute the backup members 26 of the lens insertion instrument 20. These backup fingers 26 are arcuate in cross-section with facing concave sides and have free front ends 26a. The backup member securing means 30 comprise resilient hook-like latches 64 integrally joined to the upper edges of the backup fingers. Depending from the under side of the holder body 60 a short distance rearwardly of its front end is a tapered or dovetailed key 66 whose transverse cross-section is the same in size and shape as the lower dovetailed portion 58a of the capsule key 58. At the underside of the holder body 60, between its front end and the front end of the holder key 66, is a slot 68 which opens thru the front end of the holder body and is sized and shaped to slidably receive the upper portion 58b of the capsule key 58 for aligning the lens insertion capsule 48 and capsule holder 46 about and along their common axis in the manner described below.

The actuating means 32 of the lens insertion instrument 20 comprises an insertion capsule actuator including a lever 70 of arcuate transverse cross-section disposed above the capsule holder body 60 with the front end of the lever projecting a short distance over the holder cutout 62. The rear end of the lever is recessed to form ears 74 which straddle and are pivotally attached to the holder body 60. Pivotally attached at its upper end to the underside of the front end of the lever 70 is a blade 76 whose lower end is disposed within the capsule holder body cutout 62 and shaped to form a tapered ratchet pawl 78. Also fixed to the underside of the front end of the actuator lever 70 is a leaf spring 80 which bears against the upper side of the pawl blade 76 to bias the blade counter clockwise in FIG. 16 relative to actuator lever 70 about the upper pivot axis of the blade.

The insertion capsule assembly 44 and the capsule holder 46 are joined to form the complete lens insertion instrument 20 by sliding the holder body 60 forwardly over the rear end of the capsule body 52 to the assembled positions of the capsule and holder shown in FIGS. 1, 4, 6–8, and 11. In these assembled positions, the capsule and holder are coaxially disposed with the upper portion 58b of the capsule key 58 engaging within the front slot 68 of the capsule holder body 60 and the lower tapered portion 58a of the capsule key abutting and longitudinally aligned with holder key 66 to align the insertion capsule 48 and capsule holder 46 about and along their common axis. When the capsule and holder are thus aligned, the holder backup fingers 26 straddle the capsule gripping fingers 22 with the fingers disposed in a common plane, i.e. with the backup and gripping fingers disposed for opening and closing movement in a common plane. The capsule ratchet teeth 56a and the plunger ratchet teeth 59 are exposed thru the cutout 62 in the capsule holder body 60 for engagement by the pawl 78 of the capsule actuator 32. The lower tapered portion 58a of the capsule key 58 is longitudinally aligned with the holder key 66 to form with the holder key one continuous key of uniform cross-section.

As will appear from the ensuing description, the assembled positions of the lens insertion capsule assembly 44 and the capsule holder 46 shown in FIGS. 1, 4, 6–8, and 11 constitute initial relative positions which the assembly and holder occupy in use of the instrument. In these initial relative positions, the tip portions 24 of the capsule lens gripping fingers 22 project beyond the free ends 26a of the backup fingers 26 a distance which is less than the length, and preferably about one third of the length, of the tip portions from their outer ends to the gripping finger notches 54. Accordingly, the gripping fingers 22 including their tip portions 24 are disposed between and supported against outward deflection by the backup fingers, as shown. Further, in the initial assembled positions of the capsule assembly 44 and capsule holder 46, the capsule plunger 50 is retracted rearwardly relative to the capsule 48 so that the front ends of their rows of ratchet teeth 59, 56a are aligned, and the longer ratchet tooth row on the plunger extends some distance rearwardly of the capsule ratchet tooth rows. Both the capsule and plunger are retracted rearwardly relative to the capsule holder so that the capsule and plunger ratchet teeth are exposed thru the capsule holder opening 62, and the holder actuator pawl 78 engages the front capsule and plunger ratchet teeth.

The capsule actuating pawl 78 and the ratchet teeth 56a, 59 on the insertion capsule 48 and capsule plunger 50 are shaped to form a ratchet mechanism which is operable by alternate depression and release of the actuating lever 70 to extend and retract the insertion capsule and plunger relative to one another and to the capsule holder 46. Thus, assuming that the capsule 48, plunger 50, and capsule holder 46 are in their initial assembled positions of FIGS. 3, 6–8, and 11, depression and release of the lever intermittently engages the pawl with both the capsule and plunger ratchet teeth 56a and 59 to extend the capsule and plunger in unison relative to the capsule holder until the pawl enters the recesses 56b at the rear ends of the rows of capsule ratchet teeth 56a. Continued depression and release of the actuator lever then engages the actuator pawl with the plunger ratchet teeth 59 only to extend the plunger relative to the capsule and capsule holder until the pawl enters the recess 59a at the rear end of the row of the plunger ratchet teeth. Release of the actuator lever 70 this point causes the actuator spring 80 to urge the pawl 78 rearwardly against the rear walls of the capsule and plunger recesses 56b, 59a to first retract the plunger relative to the capsule and then retract the capsule and plunger in unison relative to the capsule holder to their initial relative positions.

As mentioned earlier, the invention also provides an instrument package including a tray 36 which is constructed and arranged to support the lens insertion instrument 20 and an unfolded intraocular lens 28 to be folded and gripped by the instrument for insertion into a patient's eye. Two versions 34a (FIG. 2A) and 34b (FIG. 2B) of this instrument package are illustrated. The instrument package 34a of FIG. 2A will be described first.

The tray 36 of instrument package 34a includes an elongate base 82 with a bottom wall 83. Along the longitudinal edges of the bottom wall are upstanding edge walls 84 which extend leftward from the right end of the bottom wall in FIG. 2A a distance of about two-thirds its length. Extending across the left end of the bottom wall is a relatively thick upstanding end wall 86. The right hand side of this end wall has a central recess 86a on the longitudinal centerline of the tray and serations 86b at opposite sides of the central recess which lie along arcs that are centered about points P situated laterally inward of and close to the left ends of the edge walls 84. Entering the upper side of the bottom wall 83 between the end wall 86 and the adjacent ends of the edge walls 84 are shallow tapered recesses 88 which open edgewise thru the adjacent longitudinal edges of the bottom wall 83 and have rounded apices coaxially situated at the center points P. Directly opposite the end wall recess 86a is a generally spherically curved recess 90 in the bottom wall 83 having its center on the longitudinal centerline of the tray. Extending longitudinally thru the bottom wall along this centerline from the right end of the bottom wall to a point between the right end and the recess 90 is an upwardly opening dovetailed slot or keyway 92. The transverse cross-section of this keyway is sized and shaped to slidably receive the capsule holder key 66 and the lower portion 58a of the insertion capsule key 58.

As mentioned earlier, the tray 36 includes closure means 38 for closing the backup members or fingers 26 and thereby the lens gripping members or fingers 22 of the lens insertion instrument 20 when it is positioned on the tray. These closure means comprise a pair of backup finger closure members 94 positioned within the edge recesses 88 of the tray base 82. Each closure member has a generally tapered body 96 with a projecting tongue 98 which is pivoted to the bottom wall 83 of the base at the center points P of curvature of the arcs along which lie the serrations 86b on the base end wall 86. The closure members 94 have outer sides which project outwardly thru the spaces between the tray base edge walls 84 and end wall 86. As explained below, during use of the instrument package, finger pressure is exerted on these projecting sides of the closure members 94 to rotate them inwardly from their outer retracted positions of FIGS. 3 and 4 to their inner extended positions of FIG. 5 to close the gripping and backup fingers 22, 26 of the insertion instrument 20 when it is positioned on the tray 36. The closure members 94 have resilient pawls 100 which engage the tray end wall serrations 86b to resist outward rotation of the members and thereby retain the members in their inwardly extended positions.

Overlying the tray base 82 is a top plate 102 which is secured to the base by screws 104 and is preferably transparent. In the underside of the top plate is a recess 106 like and aligned with the base recess 90. The top plate overlies only the left hand end of the base up to the left ends of the base edge walls 84.

In addition to the tray 36, the instrument package 34a includes a foldable intraocular lens 28 and a lens insertion capsule assembly 44 positioned on the tray. The capsule assembly is positioned on the tray by inserting the lower portion 58a of its key 58 into the open right end of the keyway 68 and sliding the key to the left end of the keyway to locate the capsule assembly in its packaged position of FIG. 3. In this position, the capsule lens gripping fingers 22 are open and situated between the retracted backup finger closure members 94.

The lens 28 has a central lens portion 28a and diametrically opposed haptics 28b. The lens is lightly confined, in its normal unfolded lens configuration, between the tray base bottom wall 83 and top plate 102 with its lens portion 28a seating within the base and top wall recesses 86a, 106 and its haptics 28b extending in opposite directions along the longitudinal centerline of the tray. This instrument package comprising the tray, capsule assembly, and lens may be sterilized and sealed within an envelope 108 or the like to preserve the sterile condition of the package until the package is opened in the operating room, as described below.

The manner in which the lens insertion instrument 20 and instrument package 34a are used will now be described. Assuming that the instrument package is sealed in a sterile condition within the envelope 108 or the like, the sealed package is opened in the operating room to access the sterile insertion capsule assembly 44 on the package tray 36 preferably just before the lens 28 on the tray is to be inserted into the patient's eye. The insertion capsule holder 46 is provided separately to the operating room in a sterile condition. After the instrument package is opened, the sterile insertion capsule holder 46 is engaged with the sterile capsule assembly 44 while the latter is still on the tray 36 by inserting the key 66 of the capsule holder into the open right hand end of the tray keyway 92 and sliding the holder forwardly toward the capsule assembly until the holder body 60 slides over the capsule body 52 to their initial assembled positions of FIGS. 4, and 6–8. The capsule assembly and capsule holder then form a complete lens insertion instrument 20. As noted earlier, in these initial assembled positions of the capsule assembly 44 and the capsule holder 46, the capsule key 58 enters the holder slot 68 and abuts the front end of the holder key 66 to align the insertion capsule 48 and the capsule holder along and about their common longitudinal axis.

As explained earlier, when the capsule assembly 44 and capsule holder 46 are thus aligned, the open holder backup fingers 26 straddle the open capsule lens gripping fingers 22 with the gripping and backup fingers disposed in a common plane, that is with the fingers disposed for opening and closing movement in a common plane. It was also explained that when the insertion capsule assembly 44 is positioned on the tray 36, the plane of its lens gripping fingers 22, that is the plane of opening and closing movement of these fingers, parallels the bottom wall 83 of the tray. Accordingly, when the insertion capsule assembly 44 and capsule holder 46 are joined on the tray 36 to form the insertion instrument 20, the open capsule gripping fingers 22 straddle the lens 28 on the tray, and the open holder backup fingers 26 straddle the gripping fingers with the gripping and backup fingers disposed in a common plane parallel to the bottom wall 83 of the tray. The ratchet teeth 56a, 59 on the capsule 48 and capsule plunger 50 are exposed thru the opening 62 in the capsule holder 46 for engagement by the holder ratchet pawl 78.

After this engagement of the capsule holder 46 and the capsule assembly 44, the finger closure members 94 on the tray 36 are pressed inwardly toward one another and against the holder backup fingers 26 to close these fingers and thereby the capsule lens gripping fingers 22. Engagement of the pawls 100 on the closure members with the serrations 86b on the tray end wall 86 retains the closure members in their inner extended positions. During their closure by inward extension of the closure members 94, the gripping fingers 22 squeeze the lens 28 between their tip portions 24 and fold the lens in half, as shown in FIGS. 5 and 9. Upon arrival of the gripping fingers in their closed positions, their latches 64 engage to retain these fingers closed with the folded lens 28 gripped between their tip portions 24 and with one lens haptic projecting a short distance beyond the tip portions, as shown in FIG. 5. The top plate 102 of the tray 36 is preferably transparent to permit observation of this lens folding and gripping operation which may be performed by the surgeon or an assistant. The lens insertion instrument 20 with its gripped folded lens 28 is then removed from the tray 36 by sliding the instrument along the keyway 68 to its open end.

The folded lens 28 now stores elastic strain energy which causes the lens to exert outward pressure against the gripping finger tip portions 24. The gripping finger notches 54 are sized to weaken the gripping fingers 22 to an extent such that this pressure of the folded lens against their tip portions is sufficient to separate the tip portions by bending them outwardly at the notches. At this time, however, the free ends of the backup fingers 26 engage the gripping finger tip portions 24 and support them against separation by the outward pressure of the folded lens.

The instrument 20 is now manipulated by the surgeon to insert its gripped folded lens 28 into a patient's eye. The manner in which the instrument is used to insert the lens into the eye will be explained by reference to FIGS. 11–16 and by setting forth the successive lens insertion steps which the surgeon performs with the instrument. These successive lens insertion steps are as follows.

(1) The projecting lens haptic 28b and projecting gripping finger tip portions 24 are inserted, projecting haptic first, into the patient's eye thru a corneal incision 42, as shown in FIG. 11. An advantage of this invention is that the incision 42 may be a relatively small (i.e. 3 mm) incision such as that used for a prior cataract extraction by the phacoemulsification procedure.

(2) The capsule actuating lever 70 on the capsule holder 46 is repeatedly depressed and released to intermittently engage the actuator pawl 78 with the ratchet teeth 56a, 59 on the insertion capsule 48 and plunger 50, as shown in FIG. 11a and 16, and thereby extend the capsule and plunger in unison relative to the capsule holder 46 until the pawl engages in the recess 56b at the rear end of the capsule ratchet teeth. This action extends the tip portions 24 of the capsule gripping fingers 22 and the gripped folded lens further beyond the free ends of the backup fingers 26 and further into the eye to the positions of FIGS. 12 and 12A. In these positions, the capsule gripping finger notches 54 are situated just beyond the free ends of capsule holder backup fingers 26 and the entire length of the gripping finger tip portions 24 project beyond the free ends of the backup fingers. The gripping finger tip portions are now unsupported by the backup fingers, and the outward strain energy pressure of the folded lens 28 against the tip portions commences to bend the tip portions outwardly at the gripping finger notches 54, therby gradually spreading the tip portions and releasing their grip on the lens. The lens now commences to gradually unfold.

(3) The insertion capsule actuating lever 70 continues to be depressed and released. At this time, however, since the actuator pawl 78 engages in the recess 56b at the rear of the insertion capsule ratchet teeth 56a but still engages the ratchet teeth 59 on the capsule plunger 50, continued depression and release of the actuating lever extends the plunger relative to both the lens insertion capsule 48 and the capsule holder 46 until the pawl enters the recess 59a at the rear end of the plunger ratchet teeth while the capsule and holder remain in their relative positions of FIGS. 12, 12A. The extending plunger engages the lens 28 in the position of FIGS. 13, 13A and nudges the now unfolding lens to its position of FIG. 14 at the free ends of the now spreading gripping fingers tip portions 24. This action releases or ejects the unfolding lens into the eye as the gripping finger tip portions 24 continue to spread to release their grip on the lens.

(4) The capsule actuating lever 70 is released to permit the actuator spring 80 to bias the lever and its pawl blade 78 to their normal positions, as indicated by the broken lines in FIG. 16. During this spring return of the capsule actuator, the rear side of its pawl 78 engages the rear wall of the plunger recesses 59a and then the rear wall of the capsule recess 56b to first retract the capsule 48 relative to the plunger 50 and capsule holder 46 and then both the plunger and capsule in unison relative to the holder to the positions of FIGS. 15, 15A. This action recloses the now separated gripping finger tip portions 24 to permit the instrument to be withdrawn from the patient's eye.

(5) The instrument is withdrawn from the patient's eye, as shown in FIG. 15.

According to the preferred practice of the invention, the lens insertion capsule assembly 44 and the instrument package tray 36 are disposed of after use while the capsule holder 46 is saved for reuse. To this end, the tray, insertion capsule 48, and plunger 50 are preferably molded from a suitable plastic. The capsule holder is preferably fabricated from stainless steel or other suitable metal. Obviously, of course, the tray and capsule assembly may be made reusable or the capsule holder as well as the tray and capsule assembly may be made disposable, if desired.

The same applies to the elements of the instrument package 34b of FIG. 2B. This instrument package is identical to the instrument package 34a of FIG. 2A except that the package 34b includes the complete lens insertion instrument 20 instead of only the insertion capsule assembly 44. The instrument package 34b and its lens insertion instrument 20 are sterilized, sealed, and used in the same way as the package 34a except that in the case of the package 34b, the necessity of joining the capsule assembly and capsule holder in the operating room after opening the package is eliminated.

In the context of this invention, the instrument package 34a in combination with the insertion capsule holder 46, and the instrument package 34b constitute surgical aids for inserting or implanting a foldable intraocular lens into a patient's eye.

Thus there has been shown and described a novel intraocular lens insertion device which fulfills all the objects and advantages sought therefor. Many changes, modifications, variations and other uses and applications of the subject invention, will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

I claim:

1. A surgical aid for inserting a foldable intraocular lens into a patient's eye thru an corneal incision with the lens in a folded configuration and then releasing the lens within the eye for return of the lens to its normal unfolded lens configuration by elastic strain energy stored in the folded lens, said surgical aid comprising:

a lens insertion instrument including lens gripping members having slender lens gripping portions and movable away from one another to open positions wherein said gripping portions are spaced to straddle a foldable intraocular lens in its normal unfolded configuration and toward one another to closed positions to fold the lens and then grip the folded lens between said gripping portions; backup members straddling said gripping members and movable away from one another to open positions wherein said backup members are spaced to straddle said gripping members in their open positions and toward one another to closed positions wherein said backup members retain said gripping members in their closed positions; means for securing said backup members in their closed positions thereby to secure said gripping members in their closed positions; and actuating means operable by the instrument user for extending said gripping portions of said gripping members beyond said backup members to permit insertion of said gripping portions into the patient's eye and separation of the gripping portions within the eye;

a tray for removably receiving said lens insertion instrument with said backup members and said lens gripping members in their open positions and removably receiving a foldable intraocular lens in its normal unfolded lens configuration in a position between said gripping portions of the open lens gripping members of said instrument;

closure means for closing said backup members to close said lens gripping members while the insertion instrument is positioned on said tray, thereby to fold and then grip said lens between said gripping portions of said gripping members; and wherein said insertion instrument is removable from said tray with the folded lens gripped between said lens gripping portions of said lens gripping members for manipulation and operation of said actuating means by a user of the instrument to extend said gripping portions of said gripping members and a folded lens gripped thereby into the patient's eye thru a corneal incision and release the folded lens within the eye.

2. A surgical aid according to claim 1 wherein:
said insertion instrument comprises a lens insertion capsule including said lens gripping members, and a capsule holder releasibly engagable with said capsule to form said instrument and including said backup members, said actuating means, and said backup member securing means;
said capsule is situated on said tray with its lens gripping members in their open positions;
said capsule holder is operatively engagable with said capsule while said capsule is on said tray to form said instrument with said backup members open and straddling the open lens gripping members, said backup member closure means are then operable to close said backup members and thereby also said gripping members to fold and grip a lens positioned on the tray, said instrument is thereafter removable from said tray with the gripped folded lens for insertion of the lens into the patient's eye, and said capsule holder is removable from said capsule after insertion of the lens for disposal of said capsule and reuse of said capsule holder.

3. A surgical aid according to claim 2 wherein:
said surgical aid includes an unfolded lens positioned on said tray between the open gripping fingers of said capsule;
said tray, capsule, and unfolded lens positioned on the tray are sterilized;
said surgical aid further includes means sealing said tray, capsule, and unfolded lens to form an instrument package whose sterile condition is preserved until the package is opened; and
said capsule holder is operatibely engagable with said capsule to form said instrument after said package is opened.

4. A surgical aid according to claim 1 wherein:
said insertion instrument is positioned on said tray with its lens gripping members in their open positions; and
said backup member closure means are operable to close said backup members and thereby also said gripping members to fold and grip a lens positioned on the tray, and said instrument is thereafter removable from said tray with the gripped folded lens for insertion of the lens into the patient's eye.

5. A surgical aid according to claim 4 wherein:
said surgical aid includes an unfolded lens positioned on said tray between the open lens gripping members of said insertion instrument;
said tray, lens insertion instrument, and unfolded lens positioned on the tray are sterilized; and
said surgical aid further includes means sealing said tray, capsule, and unfolded lens to form an instrument package whose sterile condition is preserved until the package is opened to access said instrument for use.

6. A surgical aid according to claim 1 wherein:
said lens gripping members comprise pivotal lens gripping fingers having tip portions which constitute said lens gripping portions and are rotatable away from and toward one another during opening and closing movement of said gripping members;
said backup members comprise pivotal backup fingers having free end portions which straddle said lens gripping fingers and are rotatable away from and toward one another during opening and closing movement of said backup members; and
said gripping finger tip portions extend beyond the free ends of said backup fingers when said gripping fingers and backup fingers occupy their closed positions.

7. A surgical aid according to claim 6 wherein:
said actuating means includes means for extending said gripping fingers beyond said free ends of said backup fingers to free said gripping finger tip portions for separation and thereby release a folded lens gripped by the gripping fingers while said gripping finger tip portions are inserted into the patient's eye.

8. A surgical aid according to claim 7 wherein:
said backup member closure means comprise closure members movably mounted on said tray to straddle said backup fingers of said insertion instrument when said instrument is positioned on said tray and movable toward one another and against said backup fingers to close said backup fingers.

9. A surgical aid according to claim 8 wherein:

said insertion instrument comprises a capsule assembly and a capsule holder, said capsule assembly includes a capsule having a tubular body pivotally mounting said gripping fingers at one end with the gripping fingers extending beyond said one end of the body, and a plunger movable longitudinally in said body;

said capsule holder includes said actuating means, said backup finger securing means, and a tubular body pivotally mounting said backup fingers at one end and sized to slidably receive said capsule body in longitudinally assembled relation wherein said backup fingers straddle said gripping fingers;

said actuating means comprises user operable means mounted on said holder body and engagable with said capsule body and said plunger for sequentially (a) extending said capsule and plunger in unison relative to said backup fingers to extend said gripping finger tip portions further beyond said free ends of said backup fingers while said finger tip portions are inserted in the eye and therby free said gripping fingers for separation to gradually release a folded lens gripped between said gripping fingers, (b) extending said plunger relative to said gripping fingers to eject the folded lens from between said gripping fingers as they separate, (c) retracting said plunger relative to said gripping fingers, and (d) retracting said gripping fingers and said plunger relative to said backup fingers;

said backup finger securing means comprise latch means on said backup fingers which engage upon closure of the backup fingers to lock the latter fingers in their closed positions; and said capsule holder is engagable with said capsule assembly to form said insertion instrument by sliding said holder body endwise over said capsule body while said insertion capsule assembly is positioned on said tray, and the capsule holder is removable from said insertion capsule assembly for disposal of the capsule assembly and reuse of the actuator.

10. A surgical aid according to claim 9 wherein:

said tray, said capsule body, and said holder body have mating formations for coaxially aligning said bodies during engagement of said capsule holder with said insertion capsule assembly to form said insertion instrument and for locating said capsule assembly and said instrument relative to said tray.

11. A surgical aid according to claim 10 wherein:

said mating formations comprise a keyway in said tray and keys on said capsule and holder bodies slidable in said keyway.

12. A surgical aid according to claim 11 wherein:

said capsule assembly is situated on said tray with its lens gripping fingers in their open positions;

said surgical aid includes an unfolded lens positioned on said tray between the open gripping fingers of said capsule assembly;

said tray, capsule assembly, and unfolded lens positioned on the tray are sterilized;

said surgical aid includes means sealing said tray, capsule, and unfolded lens to form an instrument package whose sterile condition is preserved until the package is opened; and said capsule holder is operatively engagable with said capsule assembly after said instrument package is opened and while said capsule assembly is on said tray to form said instrument with said backup fingers open and straddling the open lens gripping fingers, said closure members are then operable to close said backup fingers and thereby also said gripping fingers to fold and grip the lens positioned on the tray, said instrument is thereafter removable from said tray with the gripped folded lens for insertion of the lens into the patient's eye, and said capsule holder is removable from said capsule assembly after insertion of the lens for disposal of said capsule assembly and reuse of said holder.

13. A surgical aid according to claim 11 wherein:

said insertion instrument is positioned on said tray with its lens gripping fingers in their open positions;

said surgical aid includes an unfolded lens positioned on said tray between the open gripping fingers of said insertion instrument;

said tray, insertion instrument, and unfolded lens positioned on the tray are sterilized; and said surgical aid includes means sealing said tray, capsule, and unfolded lens to form an instrument package whose sterile condition is preserved until the package is opened to access said insertion instrument for use.

14. A surgical aid according to claim 1 wherein:

said backup member closure means are mounted on said tray for movement against said backup members when said insertion instrument is positioned on said tray.

15. A surgical instrument for inserting a foldable intraocular lens into a patient's eye thru an corneal incision with the lens in a folded configuration and then releasing the lens within the eye for return of the lens to its normal unfolded lens configuration by elastic strain energy stored in the folded kens, said instrument comprising:

lens gripping members having slender lens gripping portions and movable away from one another to open positions wherein said gripping portions are spaced to straddle a foldable intraocular lens in its normal unfolded configuration and toward one another to closed positions to fold the lens and then grip the folded lens between said gripping portions; backup members straddling said gripping members and movable away from one another to open positions wherein said backup members are spaced to straddle said gripping members in their open positions and toward one another to closed positions to close said gripping members; means for securing said backup members in their closed positions and thereby securing said gripping members in their closed positions; and actuating means operable by the instrument user for extending said gripping portions of said gripping members beyond said backup members to permit insertion of said gripping portions into the patient's eye and separation of the gripping portions within the eye; and wherein said instrument is manipulatable by a user with said backup members secured in their closed positions and with a folded lens gripped between said gripping portions of said lens gripping members to extend said gripping portions and the gripped folded lens into the patient's eye thru an corneal incision and then release the folded lens within the eye.

16. An instrument according to claim 15 wherein:
said instrument comprises a lens insertion capsule including said lens gripping members, and a capsule holder releasibly engagable with said lens insertion capsule and including said backup members, said actuating means, and said securing means; and
said lens insertion capsule and capsule holder are engagable to form said instrument, and after use of the instrument said lens insertion capsule and capsule holder are separable for disposal of the lens insertion capsule and reuse of the capsule holder.

17. An instrument according to claim 15 wherein:
said lens gripping members comprise pivotal lens gripping fingers which are rotatable away from and toward one another during opening and closing movement of said gripping members and have tip portions forming said lens gripping portions;
said backup members comprise pivotal backup fingers which straddle and have free ends opposite said tip portions of said gripping fingers and are rotatable away from and toward one another during opening and closing movement of said backup members; and
said actuating means includes means for extending said insertion capsule relative to said capsule holder and thereby extending said gripping finger tip portions beyond said free ends of said backup fingers when said backup fingers and gripping fingers occupy their closed positions.

18. An instrument according to claim 15 wherein:
said actuating means includes means for ejecting a folded lens from between said lens gripping portions of said lens gripping members while said gripping portions are extended into the patient's eye.

19. An instrument according to claim 15 wherein:
said lens gripping members are adapted to occupy given initial positions relative to said backup members wherein said gripping portions of said gripping members project a certain distance beyond said backup members for insertion into the patient's eye with a folded lens gripped between the gripping portions when said backup members and gripping members occupy their closed positions; and
said actuating means includes means operable while said gripping portions and a folded lens gripped thereby are inserted into the patient's eye for extending said lens gripping members relative to said backup members from said initial positions to extended positions thereof wherein said gripping portions project a greater distance beyond said backup members into the eye and the gripping portions are separable by the elastic strain energy in the folded lens to release the lens into the eye.

20. An instrument according to claim 19 wherein:
said actuating means further includes means for ejecting a folded lens from said lens gripping portions of said lens gripping members during separation of the gripping portions resulting from extension of the gripping portions to said greater distance beyond said backup members.

21. An instrument according to claim 20 wherein:
said lens gripping members comprise pivotal lens gripping fingers which are rotatable away from and toward one another during opening and closing movement of said gripping members and have tip portions at one end which constitute said lens gripping portions;
said backup members comprise pivotal backup fingers having free end portions which straddle said gripping fingers and are rotatable away from and toward one another during opening and closing movement of said backup members; and
said gripping finger tip portions extend said certain distance beyond said free ends of said backup fingers when said backup fingers and gripping fingers occupy said initial relative positions thereof.

22. An instrument according to claim 21 wherein:
said instrument comprises a lens insertion capsule assembly and a capsule holder,
said capsule assembly includes said gripping fingers, a tubular body pivotally joined at one end to the other ends of said gripping fingers with the gripping fingers extending beyond said one end of the capsule body, and a plunger movable endwise in said capsule body,
said capsule holder includes said backup fingers, said actuating means, said backup member securing means, and a tubular body pivotally joined at one end to the other ends said backup fingers with said backup fingers extending beyond said one end of said holder body and slidably receiving said capsule body with said backup fingers straddling said gripping fingers;
said gripping finger tip portions are hinged to the adjacent portions of their respective gripping fingers for pivotal separation of said tip portions by elastic strain energy stored in a folded lens gripped between the tip portions to release the lens while said adjacent gripping finger portions remain closed;
said capsule and capsule holder have certain relative longitudinal positions wherein said backup fingers and gripping fingers are closed in said initial positions thereof and with said backup fingers engaging said gripping finger tip portions to support said tip portions against said pivotal separation;
said actuating means comprises user operable means mounted on said capsule holder body for sequentially (a) extending said capsule and plunger in unison relative to said capsule holder to extend said gripping finger tip portions further beyond said free ends of said backup fingers while said finger tip portions are inserted in the patient's eye and to extended positions wherein said tip portions are situated beyond the free ends of said backup fingers for separation of said tip portions to gradually release a folded lens positioned between said tip portions, (b) then extending said plunger relative to said capsule to eject the folded lens from between said gripping finger tip portions as they separate, (c) thereafter retracting said plunger relative to said capsule, and (d) finally retracting said capsule and plunger in unison relative to said capsule holder to reclose said gripping finger tip portions for removal of the instrument from the eye;
said backup member securing means comprise coacting latch means on said backup fingers which engage upon closure of the backup fingers to lock the backup fingers and thereby said gripping fingers in their closed positions; and
said capsule holder is removable from said capsule for disposal of said capsule assembly and reuse of said capsule holder.

23. An instrument according to claim 22 wherein:
said user operable means comprise ratchet teeth on said capsule body, ratchet teeth on said plunger, and a user-operable pawl mounted on said capsule holder for movement into and from ratcheting engagement with said capsule holder and plunger ratchet teeth to effect said sequential extension and retraction movements (a), (b), (c), and (d) of the capsule and plunger.

* * * * *